(12) United States Patent
Strauss et al.

(10) Patent No.: US 11,850,383 B1
(45) Date of Patent: Dec. 26, 2023

(54) FLOW-DIRECTED GUIDEWIRE

(71) Applicant: Next Neurovascular, LLC, San Clemente, CA (US)

(72) Inventors: Shane M. Strauss, San Clemente, CA (US); Spencer M. Strauss, San Clemente, CA (US)

(73) Assignee: Next Neurovascular, LLC, San Clemente, CA (US)

( * ) Notice: Subject to any disclaimer, the term of this patent is extended or adjusted under 35 U.S.C. 154(b) by 1109 days.

(21) Appl. No.: 16/274,069

(22) Filed: Feb. 12, 2019

Related U.S. Application Data

(60) Provisional application No. 62/629,502, filed on Feb. 12, 2018.

(51) Int. Cl.
*A61M 25/09* (2006.01)
*A61M 25/01* (2006.01)
*A61M 25/00* (2006.01)

(52) U.S. Cl.
CPC ........ *A61M 25/09* (2013.01); *A61M 25/0125* (2013.01); *A61M 2025/0042* (2013.01); *A61M 2025/09175* (2013.01)

(58) Field of Classification Search
CPC .............. A61M 25/09; A61M 25/0125; A61M 2025/0042; A61M 2025/09175
See application file for complete search history.

(56) References Cited

U.S. PATENT DOCUMENTS

| | | | |
|---|---|---|---|
| 5,730,733 A | 3/1998 | Mortier et al. | |
| 5,906,618 A | 5/1999 | Larson | |
| 9,162,039 B2 | 10/2015 | Hoganson et al. | |
| 2007/0244413 A1* | 10/2007 | Biggins | A61M 25/09 |
| | | | 600/585 |

FOREIGN PATENT DOCUMENTS

| | | | | |
|---|---|---|---|---|
| DE | 3607295 A1 * | 9/1987 | ........ | A61M 25/0125 |
| WO | WO-2008021497 A1 * | 2/2008 | ............ | A61M 25/09 |

* cited by examiner

*Primary Examiner* — Etsub D Berhanu
*Assistant Examiner* — Samuel C Kim
(74) *Attorney, Agent, or Firm* — Crockett & Crockett, PC; K. David Crockett, Esq.

(57) ABSTRACT

A flow-directed guidewire for use in the cerebral vasculature. The flow-directed guidewire includes a guide wire with a floppy distal end (the remainder of the guide wire is sufficiently stiff to be pushable though long segments of the vasculature) and a flow-directed structure disposed on the distal tip of the distal end of the guide wire.

7 Claims, 8 Drawing Sheets

FLOW-DIRECTED GUIDEWIRE

This application claims priority to U.S. Provisional Application 62/629,502, filed Feb. 12, 2018.

FIELD OF THE INVENTIONS

The inventions described below relate to the new field of flow directed guidewires for the cerebral vasculature.

BACKGROUND

Various flow-directed devices have been proposed for use in larger blood vessels of the body, to facilitate navigation of the devices through the vasculature to the heart or peripheral blood vessels. The flow directed devices of the prior art include catheters with balloon tips, catheters with extremely distal segments which are very floppy, and a guide wire with parachute-like "sails," which are all susceptible to being carried along the flow of blood within blood vessels to aid in advancing the tip of the device through the vasculature. An improved structure is needed to facilitate flow-directed navigation of a guidewire through the very small-diameter blood vessels of the brain.

SUMMARY

The devices and methods described below provide for access to tortuous vasculature, such as the arteries and blood vessels of the brain. The flow-directed guidewire includes a guide wire with a floppy distal end (vis-à-vis the remainder of the guide wire which is sufficiently stiff to be pushable though long segment of the vasculature) and a flow-directed structure disposed on the distal tip of the distal end of the guide wire. The flow-directed structure is designed to be carried through tortuosities in the vasculature by blood flow, and to be pushed through the vasculature by the flow of blood over the flow-directed structure.

DETAILED DESCRIPTION OF THE INVENTIONS

Figure 1:
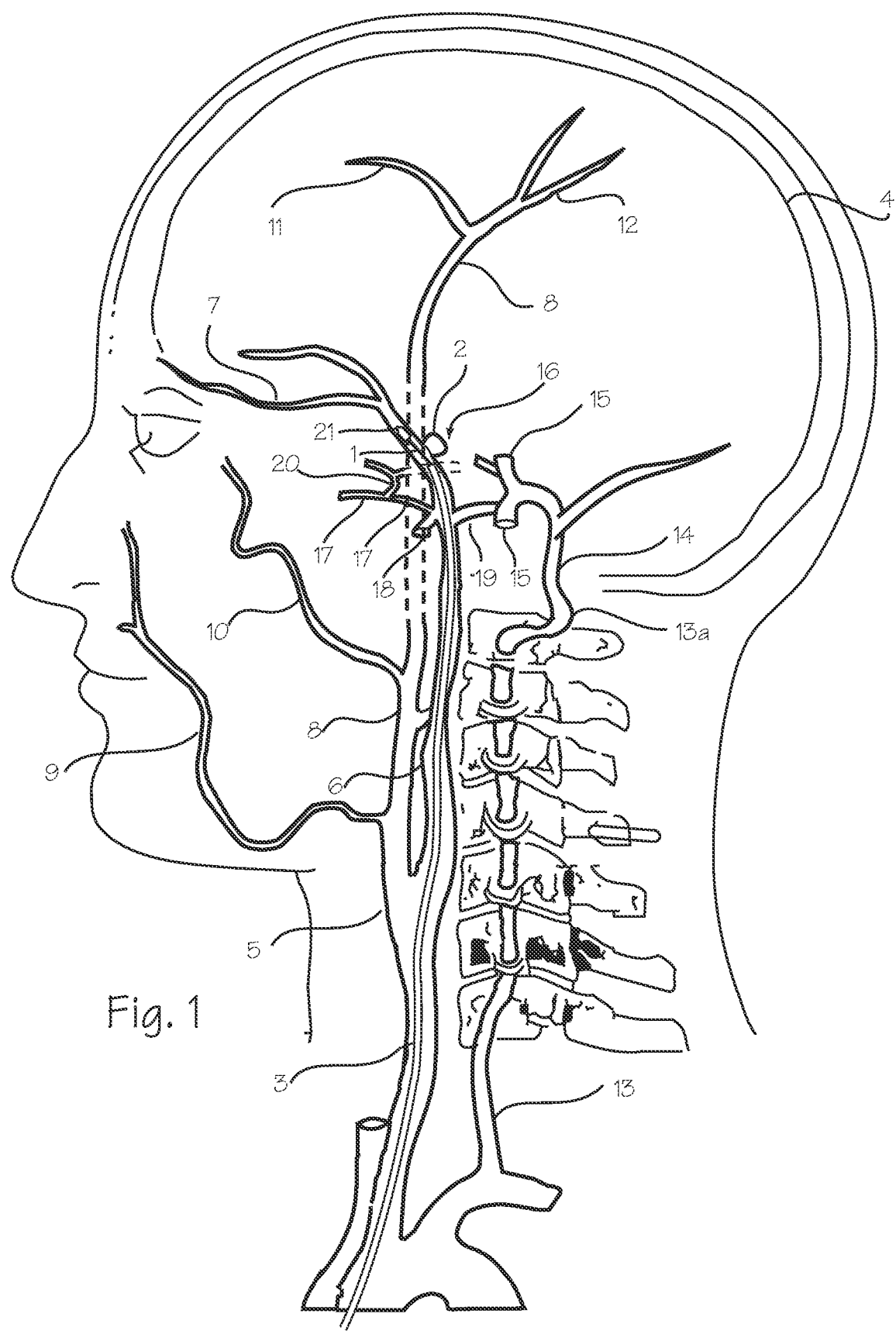
FIG. 1 is a schematic diagram of the vasculature of the brain showing the placement of a flow directed guidewire.

FIG. 1 shows the vasculature of the brain in sufficient detail to illustrate the use of the flow directed guidewire. The flow directed guidewire 1 is shown in an exemplary placement. The flow directed guidewire is shown in an exemplary placement, proximate a vascular defect 2, and disposed for much of its length in guide catheter 3. The neuro-vasculature, which is the intended environment of use for the embolic implant, supplies the brain 4 with blood through the carotid and the vertebral arteries on each side of the neck. The important arteries include the common carotid artery 5 in the neck and the internal carotid artery 6 which supplies the ophthalmic artery 7. The external carotid 8 supplies the maxillary artery 9, the middle meningeal artery 10, and the superficial temporal arteries 11 (frontal) and 12 (parietal). The vertebral artery 13 supplies the basilar artery 14 and the cerebral arteries including the posterior cerebral artery 15 and the circle of Willis indicated generally at 16. The siphon 13a of the vertebral artery appears in the intra-cranial vasculature on the vertebral approach to the Circle of Willis. Also supplied by the internal carotid artery are the anterior cerebral artery 17 and the middle cerebral artery 18, as well as the circle of Willis, including the posterior communicating artery 19 and the anterior communicating artery 20. These arteries typically have an internal diameter of about 1 mm to 5 mm, most commonly from 2-4 mm. Although the schematic shows an idealized version of vasculature, the vasculature is actually quite tortuous, with many twists and turns, that must be traversed to get the distal tip of any catheter to a target location. In FIG. 1, the flow directed guidewire 1 is shown threaded through the common carotid artery 5 and the internal carotid artery 6, which will be a common access pathway for intracerebral catheters, with flow-directed structures 21 disposed distal to the neck of an aneurysm 22 having been carried across the neck by blood flow within the arteries. Defects in any of the arteries or veins of the brain may be accessed with the flow-directed guidewire described in this application.

Figure 2:
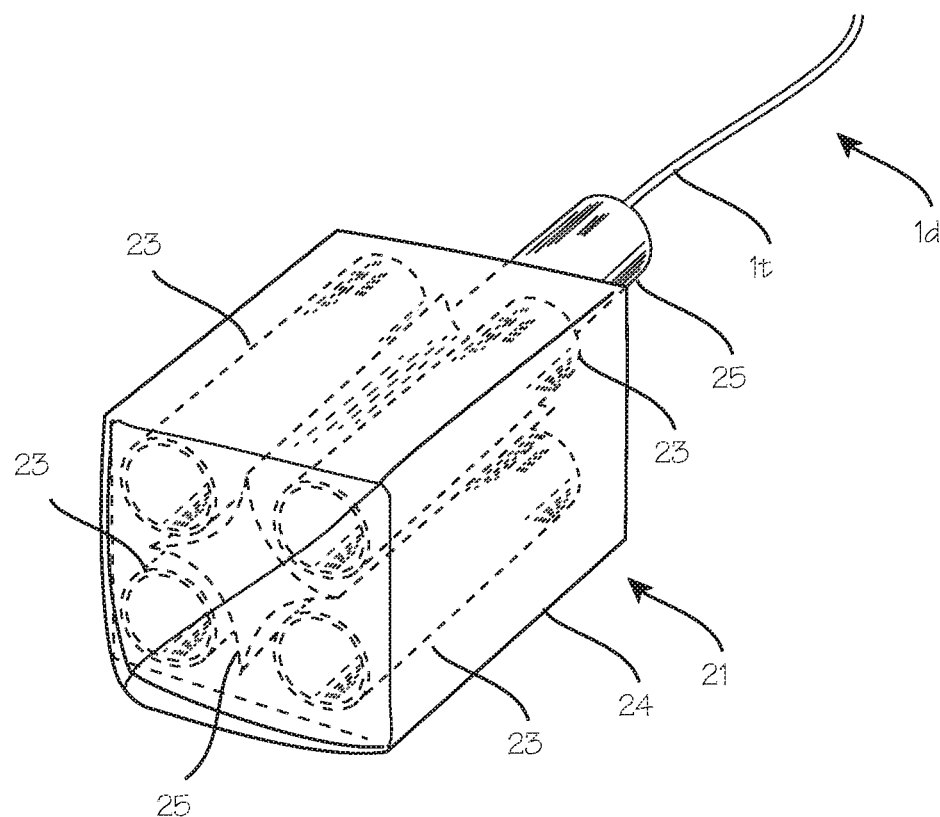
FIG. 2 illustrates a flow-directed structure of a flow-directed guidewire.

FIG. 2 illustrates a flow-directed structure of a flow-directed guidewire. The flow-directed structure 21 is disposed at the distal end of the guidewire 1, at the very distal tip of the guidewire. In this embodiment, the flow-directed structure comprises several cylinders 23 disposed about the distal tip 1t of the guide wire, with the long axis of the cylinders parallel to the long axis of the guidewire in the region of the flow-directed structure. The cylinders may be covered in a thin film 24, and a rounded or pyramidal cap may be disposed over the distal ends of the cylinders (with a single cap covering all the cylinders). The distal end of the cylinders may be open or closed, while the proximal end of the cylinders are preferably open. The distal segment 1d of the guidewire is very floppy, with just enough compression strength to be pushable within a precursor delivery catheter and within the blood vessel in the brain. The flow-directed structure of FIG. 2 is preferably the distal most structure of the guide wire and flow-directed structure assembly, and, preferably, no portion of the guidewire distal tip 1 extends distally beyond the flow-directed structure 21.

Figure 3:
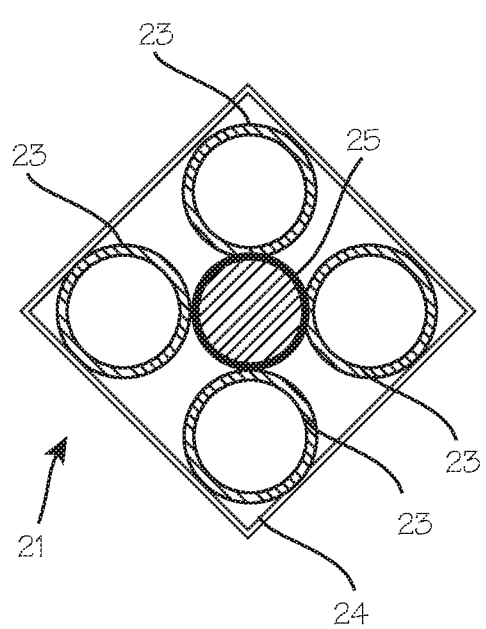
FIG. 3 is a radial cross section of the flow-directing structure of FIG. 2.

FIG. 3 is a radial cross section of the flow-directing structure of FIG. 2, showing the arrangement of the cylinders around the guidewire distal tip 1t. In this embodiment, four cylinders 23 are disposed about a central rod 25, which in turn is fixed to the distal tip 1t of the guide catheter, and the cylinders are surrounded by the thin film 24.

Figure 4:
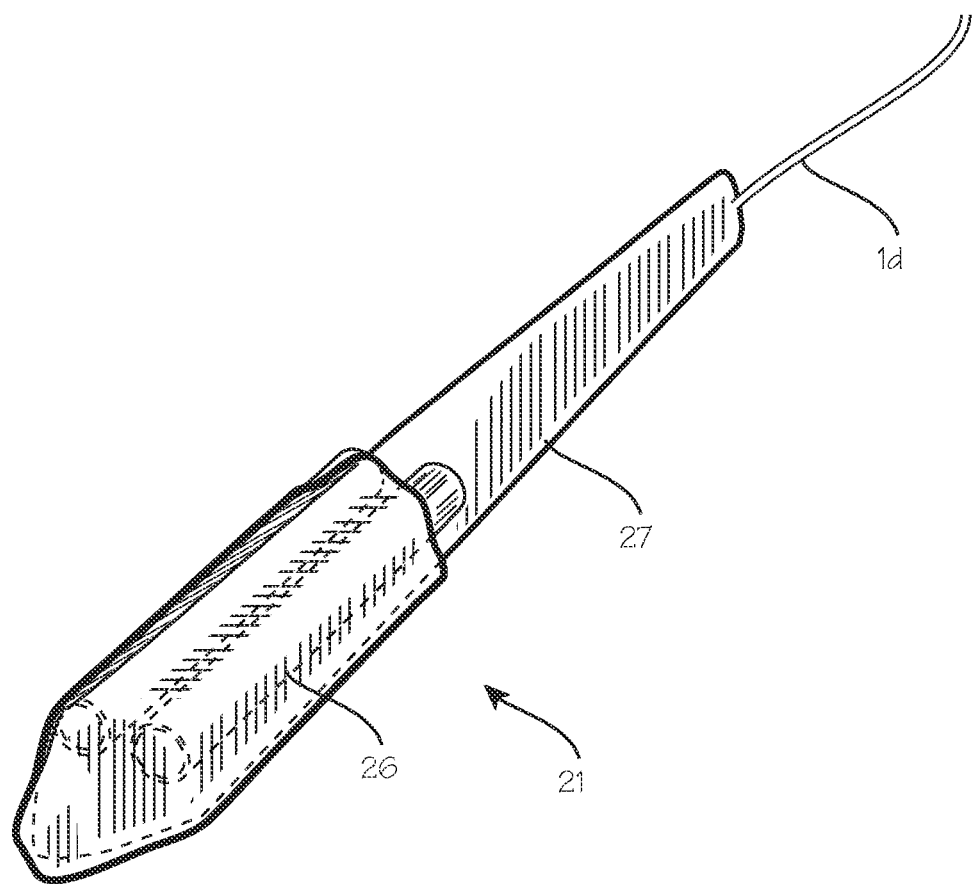
FIG. 4 illustrates an elongate flow-directed structure of a flow-directed guidewire.

FIG. 4 illustrates an elongated embodiment of a flow-directed structure disposed at the distal end of the guidewire 1, at the very distal tip of the guidewire. In this embodiment, the flow-directed structure 21 comprises two cylinders 26 disposed on either side of a flat, elongate sheet or blade 27 disposed on, or extending distally from, the distal tip it of the guide wire, with the long axis of the cylinders parallel to the long axis of the flat, elongate sheet or blade-like structure of the flow-directed structure. The cylinders may be covered in a thin film 28, and cap may be disposed over the distal ends of the cylinders (with a single cap covering all the cylinders). The distal end of the cylinders may be open or closed, while the proximal end of the cylinders are preferably open. Again, the distal segment 1d of the guidewire is very floppy, with just enough compression strength to be pushable within a precursor delivery catheter and within the blood vessel in the brain.

Figure 5:
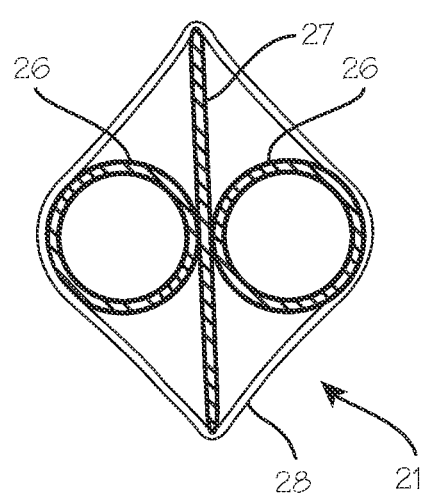
FIG. 5 is a radial cross section of the flow-directing structure of FIG. 4.

FIG. 5 is a radial cross section of the flow-directing structure of FIG. 4, illustrating the sheet 27 with cylinders 26 covered with the thin film 28.

Figure 6:
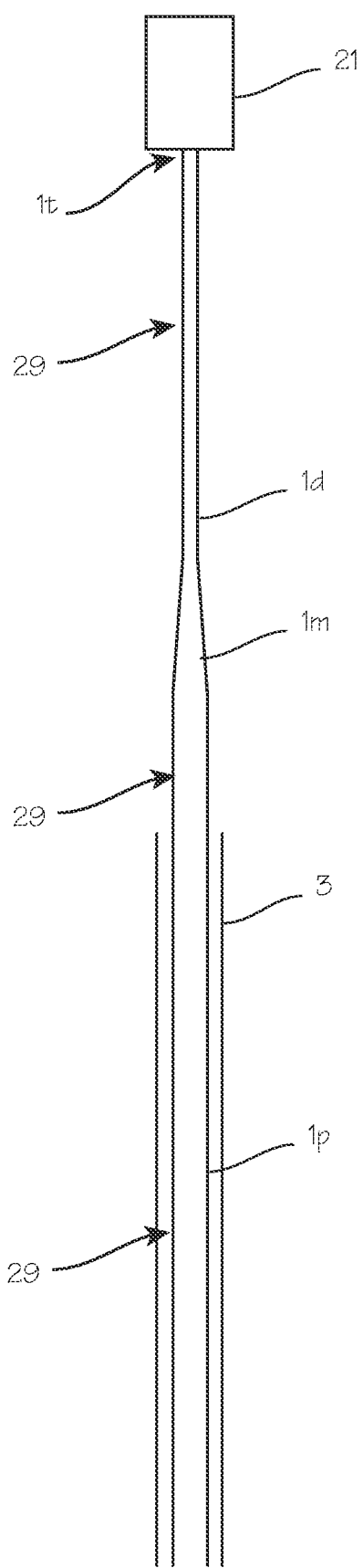
FIG. 6 is a cross section of the flow directed guidewire.

FIG. 6 is a cross section of the flow directed guidewire. The guidewire proper comprises a core wire 29, which has a diameter which decreases from the proximal segment 1p of the guide wire to the distal segment 1d of the guidewire, and the flow-directed structure 21 is disposed on the distal tip 1t of the guidewire. For use in intracerebral arteries and veins, the diameter of the distal segment is less than 0.004" (<0.10 mm) diameter and may range from 0.001 to 0.0038", (0.025 to 0.100 mm), and is preferably 0.0025" (0.06 mm). This distal segment may be about 8 cm long, and transitions into the proximal segment 1p. The diameter of the proximal segment is 0.010" or more in diameter, and 200 to 350 cm long for over-the-wire or exchange wire use, or about 135 cm for use with monorail catheters. The diameter of the flow-directed element is larger than the diameter of the distal segment, and may range from 0.008 to 0.018", with a length in the range of 0.1 to 1.0 mm (preferably about 0.5 mm). The core wire may be covered with a jacket, comprising a polymer, and may be coated with a hydrophilic coating. A intermediate segment 1m, between the distal segment 1d and the proximal segment 1p, in which the diameter transitions from the larger proximal segment diameter to the distal segment diameter, may be provided.

Figure 7:
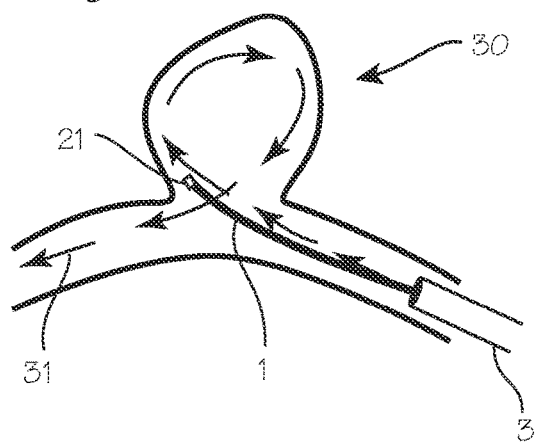
FIGS. 7 through 9 illustrates a tortuosity in the cerebral vasculature affected by a bifurcation aneurysm, and the flow directed navigation of the guide wire around the tortuosity.
Figure 8:
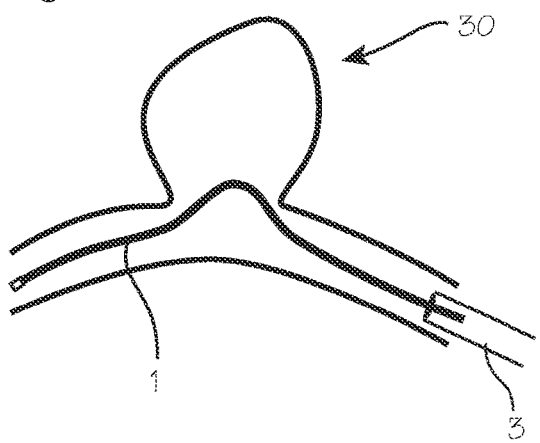
Figure 9:
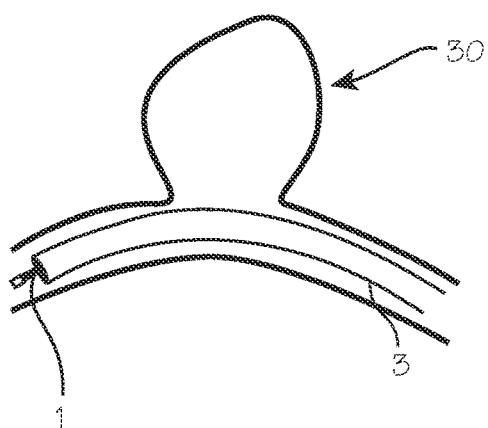

FIGS. 7 through 9 illustrate a tortuosity in the cerebral vasculature affected by a bifurcation aneurysm, and the flow directed navigation of the guide wire around the tortuosity. As shown in FIG. 7, a saccular aneurysm 30 located on a bend within the vasculature may be very difficult to pass with a normal guide wire. It may require many attempts, and quite some time, to manipulate the guide wire tip to find the entry to the distal segment of the blood vessel. However, the main volume of blood flow will be downstream, past the aneurysm, as indicted by arrow 31. As shown in FIG. 8, the distal segment and flow directed structure of the guide wire 1 are pushed distally out of a guide catheter 3, to enter the blood stream (the guide catheter may instead be withdrawn proximally while the guidewire is held longitudinal in place). After release into the blood stream, the flow directed structure will be carried distally by the blood flow, to reside in the blood vessel segment distal to the aneurysm. At this point, the guide catheter 3 is pushed distally, over the guide wire, while the guide wire is held longitudinally fixed (held at the proximal end) until the guide catheter reaches a desired target site. This is illustrated in FIG. 9. This procedure can be repeated as necessary to cross a number of tight turns in the blood vessel. When the guide catheter has been navigated to a desired target site, the guide wire is removed to clear the lumen of the guide catheter, and working catheters or various fluids can be delivered to the target site. Depending on the procedure to be performed, and the working catheters to be used, the original guide catheter 3 may be withdrawn, leaving the guide wire in place, and a second guide catheter can be inserted over the guide wire.

Figure 10:
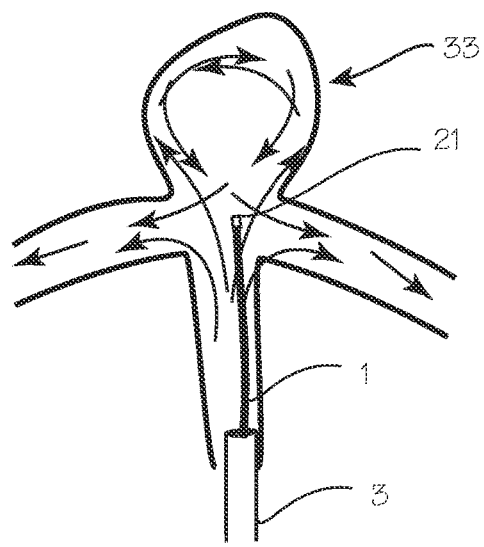
FIGS. 10 through 19 illustrate use of the guidewire to facilitate deployment of flow diverters in a vascular bifurcation with an aneurysm.
Figure 11:
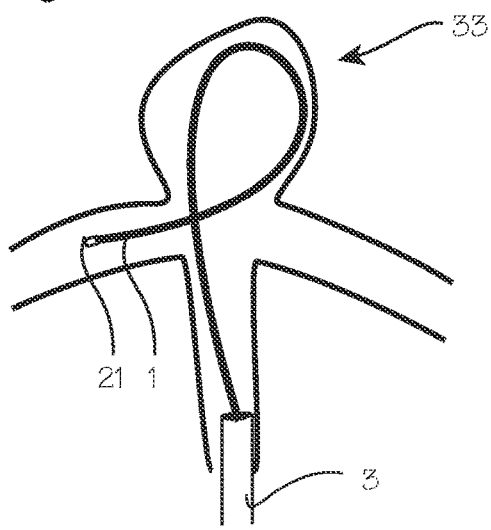
Figure 12:
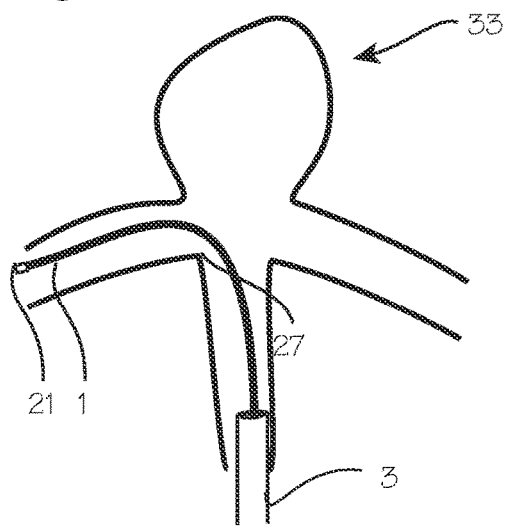
Figure 13:
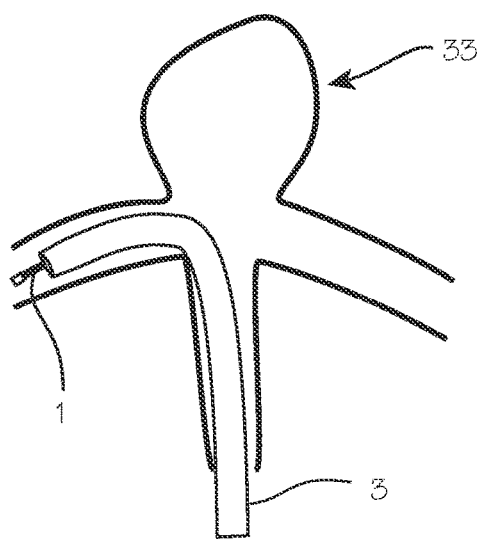
Figure 14:
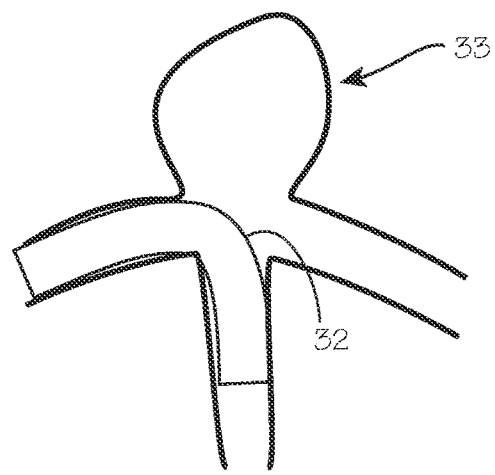
Figure 15:
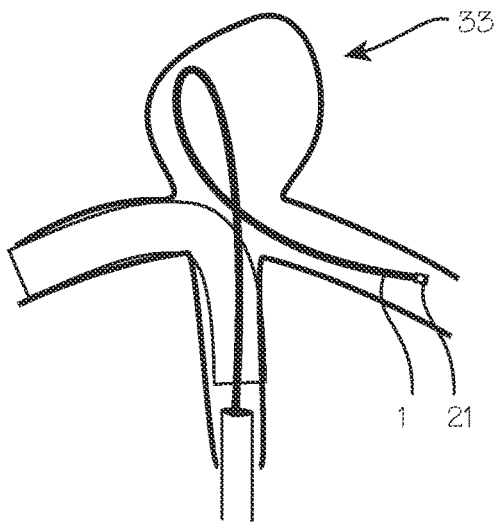
Figure 16:
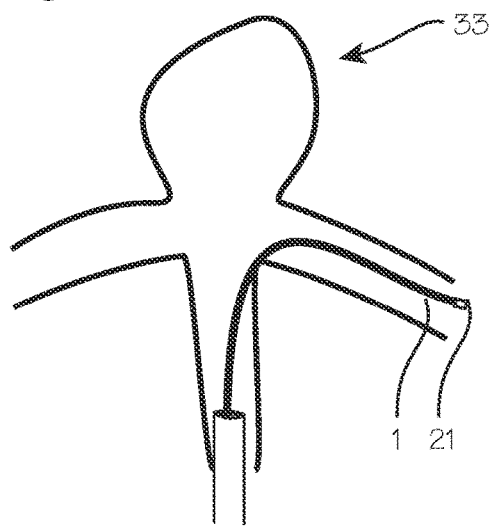
Figure 17:
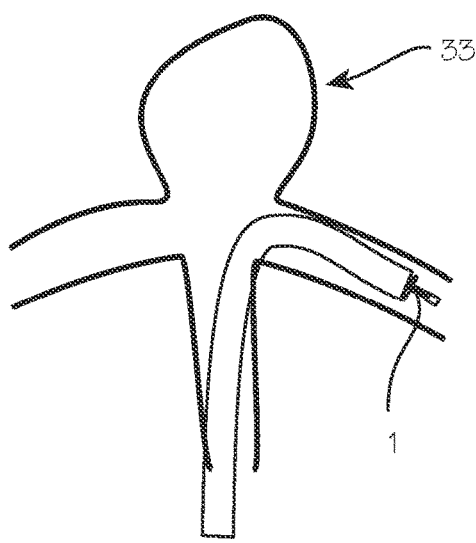
Figure 18:
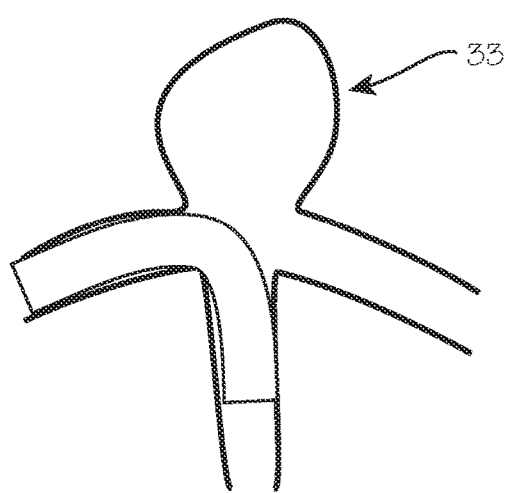
Figure 19:
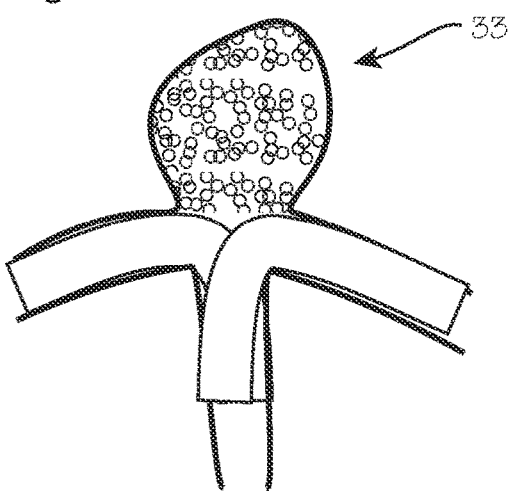

FIGS. 10 through 19 illustrate use of the guidewire. In this example, the guidewire is used to facilitate deployment of flow diverters in a vascular bifurcation with an aneurysm. FIG. 10 illustrates a saccular aneurysm, specifically a bifurcation aneurysm 33, such as basilar tip aneurysm, at the junction of an inlet artery and two outlet arteries, typically opposite the inlet of the junction. As the flow vectors illustrate, flow through the junction is turbulent, and including flow into and out of the aneurysm sac, and flow directly from the inlet artery to the outlet arteries. To gain access to one or both of the outlet arteries, the flow directed guidewire is navigated through the vasculature to the base of the bifurcation through the guide catheter (or other tortuosity). The guide wire is then pushed out of the guide catheter, or exposed by withdrawal of the guide catheter, and exposed to blood flow. With the aid of blood flow acting on the distal structure, and carrying the distal structure downstream, the guide wire will be directed down one of the outlet arteries. The surgeon can gently manipulate the guide wire distal end until the distal structure enters the desired outlet artery, as illustrated in FIGS. 11 and 12. With the guide wire positioned in an outlet artery, the surgeon can push the guide catheter, or a micro-catheter, over the guide wire into the outlet artery, as shown in FIG. 13. As shown in FIG. 14, the guide catheter (or micro-catheter) can be used to deliver a flow diverter into the first outlet artery. If desired, the procedure may be repeated contralaterally, to place a flow diverter in the second outlet artery, by routing the guide wire and guide catheter past the in-place flow diverter to access the second, contralateral outlet artery, as shown in FIG. 15, repeating the manipulation of the guide wire get the blood flow to carry the flow-directed structure to the second outlet artery as shown in FIGS. 15 and 16, then advancing the guide catheter over the guide wire as shown in FIG. 17, and delivering a second flow diverter, into the second outlet artery, as shown in FIG. 18. As shown in FIG. 19, a surgeon may choose to deliver an embolic agent into the aneurysm sac to fill the sac and prevent rupture and subsequent leakage into surrounding tissue.

Generally, the method of using the guidewire to access the cerebral vasculature of a patient includes the steps of providing a guidewire comprising the wire characterized by a proximal segment and a distal segment characterized by a longitudinal axis, the flow-directed structure disposed on the distal segment where the flow-directed structure includes a features described in the figures, and navigating the distal end of the guide wire through a guide catheter and the vasculature of the patient and into the cerebral vasculature of the patient, proximate a tortuosity of the cerebral vasculature. To take advantage of the flow-directing structure, a surgeon will expose the flow-directed structure to blood flow and allow the blood flow to carry the flow-directed structure distally in the direction of the blood flow. The method may be used to gain access to other small blood vessels in the body.

Portions of the guidewire may include coils disposed about the core wire 29, and radiopaque markers may be added at various location on the guide wire and the flow-directed structure.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A guidewire comprising:
   a wire characterized by a proximal segment and a distal segment characterized by a longitudinal axis;
   a flow-directed structure disposed on the distal segment, said flow-directed structure comprising:
   a first cylinder having an open proximal end and a closed distal end and longitudinal axis, said first cylinder extending along the distal segment of the wire, or extending distally from the distal segment of the wire, with the longitudinal axis of the first cylinder parallel to the longitudinal axis of the wire; and
   a second cylinder having an open proximal end and a closed distal end and longitudinal axis, said second cylinder extending along the distal segment of the wire, or extending distally from the distal segment of the wire, with the longitudinal axis of the second cylinder parallel to and radially displaced from the longitudinal axis of the wire.

2. The guidewire of claim 1 further comprising:
   a covering disposed about the first and second cylinders.

3. The guidewire of claim 1 further comprising:
   a distal covering disposed distally of the first and second cylinders.

4. A guidewire comprising:
   a wire characterized by a proximal segment and a distal segment characterized by a longitudinal axis;
   a flow-directed structure disposed on the distal segment, said flow-directed structure comprising:
   a flat structure characterized by a longitudinal axis, said flat structure extending distally along or distally beyond the distal segment of the wire, with a first cylinder and second cylinder disposed thereon, said first cylinder having an open proximal end and a closed distal end and a longitudinal axis, said second cylinder having an open proximal end and a closed distal end and a longitudinal axis, both of said first cylinder and said second cylinder extending along the flat structure with the longitudinal axis of each of said first cylinder and said second cylinder parallel to and radially displaced from the longitudinal axis of the flat structure.

5. The guidewire of claim 4 further comprising:
   a covering disposed about the cylinders.

6. The guidewire of claim 4 further comprising:
   a distal covering disposed distally over the cylinders.

7. A method of using a guidewire to access the cerebral vasculature of a patient, said method comprising:
   providing a guidewire comprising:
      a wire characterized by a proximal segment and a distal segment characterized by a longitudinal axis;
      a flow-directed structure disposed on the distal segment, said flow-directed structure comprising:
   a first cylinder having an open proximal end and a closed distal end and longitudinal axis, said first cylinder extending along the distal segment of the wire, or extending distally from the distal segment of the wire, with the longitudinal axis of the first cylinder parallel to and radially displaced from the longitudinal axis of the wire; and
   a second cylinder having an open proximal end and a closed distal end and longitudinal axis, said second cylinder extending along the distal segment of the wire, or extending distally from the distal segment of the wire, with the longitudinal axis of the second cylinder parallel to and radially displaced from the longitudinal axis of the wire;
   navigating the distal segment of the wire through a guide catheter and the vasculature of the patient and into the cerebral vasculature of the patient, proximate a tortuosity of the cerebral vasculature; and
   exposing the flow-directed structure to blood flow, and allowing the blood flow to carry the flow-directed structure distally in the direction of the blood flow.

\* \* \* \* \*